United States Patent [19]
Pickart

[11] Patent Number: 4,767,753
[45] Date of Patent: Aug. 30, 1988

[54] METHODS AND COMPOSITIONS FOR PREVENTING ULCERS

[75] Inventor: Loren R. Pickart, Bellevue, Wash.

[73] Assignee: ProCyte Corporation, Redmond, Wash.

[21] Appl. No.: 48,276

[22] Filed: May 11, 1987

Related U.S. Application Data

[63] Continuation-in-part of Ser. No. 699,824, Feb. 8, 1985, Pat. No. 4,665,054.

[51] Int. Cl.$^4$ ............................................ A61K 37/02
[52] U.S. Cl. ................................................... 514/18
[58] Field of Search ........................................ 514/18

[56] References Cited

U.S. PATENT DOCUMENTS 4,665,054  5/1987  Pickart .................................. 514/18

Primary Examiner—Delbert R. Phillips
Attorney, Agent, or Firm—Seed and Berry

[57] ABSTRACT

A variety of compositions suitable for use within methods for (a) reducing the formation of stomach ulcers in warm-blooded animals, (b) reducing the secretion of stomach acid in warm-blooded animals, and (c) increasing the secretion of ctyoprotective mucous in the stomach of warm-blooded animals are disclosed. The compositions include glycyl-L-histidyl-L-lysine, glycyl-L-histidyl-L-lysine: copper(II), and derivatives thereof.

12 Claims, 1 Drawing Sheet

METHODS AND COMPOSITIONS FOR PREVENTING ULCERS

CROSS-REFERENCE TO RELATED APPLICATION

This application is a continuation-in-part of pending U.S. Ser. No. 669,824 filed 2-8-85, now U.S. Pat. No. 4,665,054.

TECHNICAL FIELD

The present invention relates to the prevention of ulcers in general, and more specifically, to the use of glycyl-L-histydyl-L-lysine, glycyl-L-histidyl-L-lysine; copper(II), and derivatives thereof within a method for preventing ulcers in warm-blooded animals.

BACKGROUND ART

The development and treatment of stomach ulcers remain a major health problem despite the development of numerous anti-ulcer medications. Traditionally, digestive ulcers have been treated through neutralization of excess stomach acid or through diet and behavioral or emotional modification. Well-known stomach acid neutralizers include sodium bicarbonate, magnesium hydroxide, calcium carbonate, aluminum hydroxide, aluminum phosphate, magnesium trisilicate, and tribasic calcium phosphate. Certain polyamine methylene resins have also been tried. Attempts have also been made to inhibit the flow of gastric acid, although these attempts are characterized by rather serious side effects. More recently, a compound referred as cimetidine has been effective in stopping the secretion of stomach acid by blocking histamine sites. However, while being relatively effective in stopping acid flow, cimetidine has been found to have certain undesirable characteristics, including impairment of kidney function and mental confusion.

While certain low molecular weight compositions, such as salicylate-copper of diisopropylsalicylate-copper, have been reported to inhibit the production of stomach ulcers, these complexes tend to easily dissociate in the stomach into free copper and salicylate, which limits their practical use. In addition, these small copper complexes tend to be poorly soluble under aqueous conditions and must be administered with tissue-irritating solubilizing agents. Another such agent, the penicillamine-copper complex, often produces skin rashes and personality changes ("penicillamine psychosis").

Therefore, there is a need in the art for an improved composition for preventing the formation of ulcers. The present invention provides such a composition, and further provides other related advantages.

DISCLOSURE OF THE INVENTION

Briefly stated, the present invention discloses a variety of pharmaceutical compositions suitable for use within the methods hereinafter described: (a) a method for reducing the formation of stomach ulcers in warm-blooded animals; (b) a method for reducing the secretion of stomach acid in warm-blooded animals; and (c) a method for increasing the secretion of cytoprotective mucous in the stomach of warm-blooded animals.

The compositions described herein include glycyl-L-histidyl-L-lysine (GHL), glycyl-L-histidyl-L-lysine:copper(II), (GHL-Cu), and various derivatives of GHL-CU. The derivatives of GHL-Cu have the general formula:

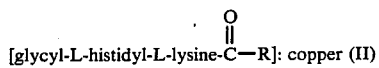

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

In addition to the derivatives described above, other chemical modifications may be made to alter the biological activity of the derivatives of the present invention. For instance, glycine may be replaced by a variety of other small amino acids, including alanine, serine, and valine. Further, the copper(II) binding affinity of the molecule may be increased by addition of an N-terminal amino acid, such as glycine, to convert glycyl-L-histidyl-L-lysine to glycyl-L-glycyl-L-histidyl-L-lysine. In addition, glycine could be added to a derivative as described above to create the corresponding tetrapeptide. The binding affinity for copper(II) of the imadazole group in the histidyl residue may be modified by substitution of 3-methylhistidine for histidine or by extending the lysyl side chains by adding additional carbon atoms to the chain.

The methods described above generally comprise administering to the animal a therapeutically effective amount of one of the compositions described above in order to effect the desired purpose. Other aspects of the present invention will become evident upon reference to the following detailed description and attached drawing.

DESCRIPTION OF THE DRAWING

The FIGURE is a photograph of rat stomachs, illustrating the ulcerations in control animals as compared to treated animals. The circled black dots in the stomach wall are stomach ulcers.

BEST MODE FOR CARRYING OUT THE INVENTION

Figure 1:
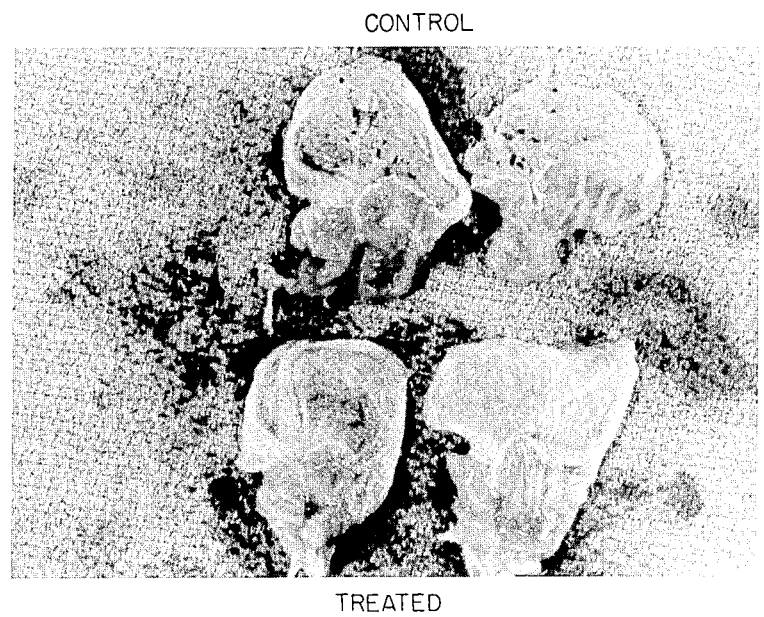

As described herein, GHL, GHL-Cu, and various derivatives thereof may be used in methods for (a) reducing the secretion of stomach acid in warm-bloded animals, (b) increasing the secretion of cytoprotective mucous in the stomach of warm-blooded animals, and (c) reducing the formation of stomach ulcers in warm-blooded animals. The derivatives of the present invention are described in detail in U.S. patent application Ser. Nos. 699,824 and 040,460, which applications are hereby incorporated by reference. The derivatives of the present invention may be prepared by esterification, by the removal of a water molecule, or by the addition of a group (either an alcohol, such as octanol, methanol, benzyl alcohol, or NH$_3$) to the carboxylic acid terminus of GHL, resulting in the formation of a more lipophilic derivative.

The overall chemical reaction in this transformation may be characterized:

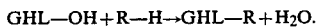

In practice, the reaction is most readily carried out by adding the R group to the amino acid lysine prior to the combination of lysine with the other two amino acids to GHL. After the formation and isolation of GHL-R, the copper(II) is chelated to the molecule to form the bioactive complex.

The overall reaction to form the more lipophilic derivatives of GHL-Cu may be characterized:

(1) lysine-OH + R—H→lysine-R + H$_2$O (2) lysine-R + blocked L-histidine→blocked L-histidine-L-lysine-R (3) blocked L-histidine-L-lysine-R + blocked-glycine→blocked glycyl-L-histidine-L-lysine-R (4) blocked glycyl-L-histidine-L-lysine-R→glycyl-L-histidine-L-lysine-R (5) glycyl-L-histidine-L-lysine-R + copper(II)→glycyl-L-histidine-L-lysine-R: copper(II).

Within preferred embodiments, GHL or a derivative of GHL and copper are present in a 1:1 ratio.

In addition to the methods described above, the results disclosed herein suggest that GHL, GHL-Cu, and derivatives thereof will also exert healing actions on other gastrointestinal diseases, such as colonic healing after anastomosis, lesions occurring subsequent to intestinal and bowel ischemia, necrotizing enterocolitis, and wounds of the mouth, throat and esophagus.

Within the present invention, it is generally preferred to administer the compositions described herein orally and in a capsule form. Methods for encapsulating compositions (such as in a coating of hard gelatin) for oral administration are well known in the art (Baker, Richard, *Controlled Release of Biologically Active Agents*, John Wiley and Sons, 1986). It is also generally preferred to administer the compositions in dosages from about 10 to 100 mg/kg of host body weight, although the dosage may be influenced by the condition of the patient. Further, it may be preferable to initially begin using a treatment of GHL-Cu, and then continue with treatment using the free peptide (GHL) with or without a small amount of copper(II).

To summarize the examples that follow, Example 1 illustrates the synthesis of glycyl-L-histidyl-L-lysine benzyl ester: copper(II). Example 2 demonstrates the synthesis of glycyl-L-histidyl-L-lysine n-octyl ester: copper(II). Example 3 illustrates (A) the synthesis of glycyl-L-histidyl-L-lysine n-stearyl ester: copper(II), and (B) its synthesis by an alternative procedure. Based upon either procedure, one skilled in the art could substitute n-palmityl alcohol (16 carbons) for the n-stearyl alcohol (18 carbons) to yield glycyl-L-histidyl-L-lysine n-stearyl ester: copper(II). Example 4 illustrates the synthesis of glycyl-L-histidyl-L-lysyl-L-propyl-L-valyl-L-phenylalanyl-L-valine: copper(II) and glycyl-L-histidyl-L-lysyl-L-valyl-L-phenylalanyl-L-valine: copper(II). Example 5 demonstrates (a) the inhibition of stomach acid accumulation, (b) the stimulation of cytoprotective mucous secretion, and (c) a reduction in the formation of stomach ulcers in warm-blooded animals.

The following examples are offered by way of illustration and not by way of limitation.

EXAMPLES

Preparation of GHL; GHL-Cu for Use in Animals

GHL was purified by dissolving, in glass, distilled water (50 mg/ml), then centrifuging at 20,000×g for 1 hour at 3° C. This removes poorly water-soluble material remaining from the synthetic procedure. The supernatent is lyophilized, then passed through a Sephadex G-10 column at 3° C. in a solvent of 0.5% acetic acid. The main peak that elutes behind the solvent front (monitored by absorption at 254 nanometers) is lyophilized to dryness. GHL-Cu was prepared by combining purified GHL with equimolar amounts of cupric acetate and sodium hydroxide, then precipitated by use of ethanol addition and low temperature by published of methods (Perkins et al., *Inorg. Chim. Acta* 67: 93–99, 1984).

Sources of chemicals

Chemicals and peptide intermediates utilized in the following examples may be purchased from the following suppliers: Sigma Chemical Co. (St. Louis, Mo.); Peninsula Laboratories (San Carlos, Calif.); Aldridge Chemical Co. (Milwaukee, Wis.); Vega Biochemicals (Tucson, Ariz.); Pierce Chemical Co. (Rockford, Ill.); Research Biochemicals (Cleveland, Ohio); Van Waters and Rogers (South San Francisco, Calif.); Bachem, Inc. (Torrance, Calif.).

EXAMPLE 1

Synthesis of glycyl-L-histidyl-L-lysine benzyl ester: copper(II)

$N^e$-benzyloxycarbonyl-L-lysine benzyl ester was dissolved in 1:1 hexane-ethyl acetate and coupled to $N^a$-t-butyloxycarbonyl-$N^{im}$-benzyloxycarbonyl-L-histidine using dicyclohexylcarbodiimide as a coupling agent. Sodium bicarbonate (10%) was added and the product extracted into the organic layer. The product, $N^a$-t-butyloxycarbonyl-$N^{im}$-benzyloxycarbonyl-L-histidyl-$N^e$-benzyloxycarbonyl-L-lysine benzyl ester, was crystallized from solution. The N-terminal group of the blocked dipeptide was removed by stirring in 50% trifluoroacetic acid in dichloromethane for 30 minutes, then vacuum evaporated. The product, $N^{im}$-benzyloxycarbonyl-L-histidyl-$N^e$-benzoylcarbonyl-L-lysine benzyl ester, was coupled to t-butyloxycarbonylglycine with dicyclohexylcarbodiimide as a coupling agent. Blocking groups were removed by catalytic hydrogenation using 10% palladium on carbon in glacial acetic acid. After lyophilization, the product, glycyl-L-histidyl-L-lysine benzyl ester, was dissolved in water and purified by ion-exchange chromatography on Dowex 50 X-4 cation-exchange resin and elution with 0.1M ammonium hydroxide, the eluate being immediately neutralized with acetic acid. A further passage through an anion-exchange column BioRex 63 at neutral pH removed breakdown products with free carboxylic acid groups.

The glycyl-L-histidyl-L-lysine benzyl ester was dissolved in water with equimolar copper acetate added. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine benzyl ester: copper(II).

EXAMPLE 2

Synthesis of glycyl-L-histidyl-L-lysine n-octyl ester: copper(II)

A mixture of $N^e$-benzyloxycarbonyl L-lysine, n-octanol, benzene, and p-toluenesulfonic acid monohydrate was refluxed overnight using a Dean-Stark trap to remove water. After cooling, dry ethyl ether was added. The solution was then allowed to precipitate at 0° C. overnight. A portion of the precipitated solid was added to 50 ml potassium carbonate solution and 50 ml dichloromethane. After extraction, the layers were separated and the organic phase washed with water and brine, then dried with anhydrous magnesium sulfate. Filtration, evaporation and purification by flash column chromatography gave n-octyl $N^e$-benzyloxycarbonyl-L-lysinate. The product was dissolved in tetrahydrofuran and mixed with $N^a$-t-butyloxycarbonyl-L-$N^{im}$-benzyloxycarbonyl-L-histidine, isobutyl chloroformate and N-methylmorpholine. After evaporation, water and ethyl acetate were added. The product was extracted into the organic phase, which was dried with anhydrous magnesium sulfate. Filtration, evaporation and purification by flash column chromatography gave n-octyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-octyl $N^{im}$-benzyloxycarbonyl-L-histidyl-$N^e$-benzyloxycarbonyl-L-lysinate. This was dissolved in tetrahydrofuran, and isobutyl chloroformate, N-methylmorpholine and benzyloxycarbonylglycine were added to form n-octyl benzyloxycarbonylglycyl-$N^{im}$-benzyloxycarbonyl-L-histidyl-$N^e$-benzyloxycarbonyl-L-lysinate. This was dissoled in glacial acetic acid and hydrogenated overnight.

The resultant n-octyl ester of glycyl-L-histidyl-L-lysine was converted to the copper complex by the addition of an equimolar quantity of copper diacetate. The pH was raised to neutrality with sodium hydroxide. The solution was centrifuged at 20,000×g for 1 hour at 3° C. to remove poorly water-soluble material. The supernatant was lyophilized to obtain glycyl-L-histidyl-L-lysine n-octyl ester: copper(II).

EXAMPLE 3

A. Synthesis of glycyl-L-histidyl-L-lysine n-stearyl ester: copper(II)

A mixture of $N^e$-benzyloxycarbonyl-L-lysine, n-stearyl alcohol, benzene, and p-toluenesulfonic acid monohydrate was refluxed overnight using a Dean-Stark trap to remove water. After cooling, dry propyl ether was added to increase the total volume sixfold. The product was allowed to precipitate at 0° C. overnight and filtered. A portion of the filtrate was added to 50 ml potassium carbonate and 50 ml dichloromethane. After extraction, the layers were separated, and the organic phase was washed with water and brine, then dried with anhydrous magnesium sulfate. Filtration, evaporation and purification by flash column chromatography gave n-stearyl $N^e$-benzyloxycarbonyl-L-lysinate. The product was dissolved in tetrahydrofuran and mixed with $N^a$-t-butyloxycarbonyl-$N^{im}$-benzyloxycarbonyl-L-histidine and isobutyl chloroformate and N-methylmorpholine. After evaporation, water and propyl acetate were added and the product was extracted into the organic phase, then dried with anhydrous magnesium sulfate. Filtration, evaporation and purification by flash column chromatography gave n-stearyl $N^a$-t-butyloxycarbonyl-$N^{im}$-benzyloxycarbonyl-L-histidyl-$N^e$-benzyloxycarbonyl-L-lysinate.

The product was dissolved in 50% trifluoroacetic acid in dichloromethane for 30 minutes, then evaporated, forming n-stearyl $N^{im}$-benzyloxycarbonyl-L-histidyl-$N^e$-benzyloxycarbonyl-L-lysinate, which was dissolved in tetrahydrofuran, isobutyl chloroformate, N-methylmorpholine and benzyloxycarbonylglycine to form n-stearyl benzyloxycarbonylglycyl-$N^{im}$-benzyloxycarbonyl-L-histidyl-$N^e$-benzyloxycarbonyl-L-lysinate. The product was dissolved in 50% trifluoroacetic acid in dichloromethane for 30 minutes, then evaporated, forming n-stearyl ester glycyl-L-histidyl-L-lysine.

The resultant molecule, glycyl-L-histidyl-L-lysine n-stearyl ester, was converted to the copper complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

B. Alternative synthesis of glycyl-L-histidyl-L-lysine n-stearyl ester: copper(II)

$N(\epsilon)$-benzyloxycarbonyl-L-lysine, n-stearyl alcohol, p-toluenesulfonic acid monohydrate, and benzene are refluxed together using a Dean-Stark trap to azeotropically remove the evolved water. After cooling to room temperature and then adding dry ethyl ether, n-stearyl $N(\epsilon)$-benzyloxycarbonyl-L-lysinate p-toluenesulfonate salt is collected by filtration, treated with 2M aqueous potassium bicarbonate solution, and extracted into dichloromethane. Evaporation gives the free amine, which is redissolved in dry tetrahydrofuran (THF) and added to a stirring solution of $N(\alpha)$-t-butyloxycarbonyl-$N(im)$-benzyloxycarbonyl-L-histidine, N-methylmorpholine, and isobutyl chloroformate in dry THF at $-15°$ C. The resulting fully protected dipeptide ester is treated with 1/1 trifluoroacetic acid/dichloromethane at room temperature, neutralized with saturated aqueous sodium bicarbonate solution, and extracted into ethyl acetate. Evaporation gives the partially deblocked dipeptide, which is redissolved in dry THF and added to a stirring solution of benzyloxycarbonylglycine, N-methylmorpholine and isobutyl chloroformate in dry THF at $-15°$ C. The formed, fully protected tripeptide ester is totally deblocked by treatment with hydrogen gas in glacial acetic acid at room temperature in the presence of Pd-C catalyst. Filtration, evaporation and purification on a microcrystalline cellulose column followed by lyophilization give the desired tripeptide ester as its triacetate salt.

The resultant molecule, glycyl-L-histidyl-L-lysine n-stearyl ester, was converted to the copper-complex by the addition of an equimolar quantity of copper diacetate. The pH was raised to neutrality with sodium hydroxide to obtain a product useful for animal studies.

By substituting n-palmityl alcohol for the n-stearyl alcohol, glycyl-L-histidyl-L-lysine n-palmityl ester may be similarly synthesized.

EXAMPLE 4

Synthesis of glycyl-L-histidyl-L-lysyl-L-prolyl-L-valyl-L-phenylalanyl-L-valine: copper(II) and of glycyl-L-histidyl-L-lysyl-L-valyl-L-phenylalanyl-L-valine: copper(II)

These peptides are synthesized by standard solid-phase methods common to the peptide field (J. Stewart and J. Young, *Solid Phase Peptide Synthesis*, Pierce Chemical Co., 1984). Briefly stated, Boc-Val-O-Resin was sequentially coupled with other blocked amino acids using dicyclohexylcarbodiimide as a reaction agent. Protected amino acids, resins for solid-phase synthesis, and coupling agents were obtained from Peninsula Laboratories, San Carlos, Calif. Blocked amino acids are added in sequential order to obtain the desired peptide. The final peptide is deblocked using hydrogen fluoride. The final peptide is dissolved in 0.5% acetic acid and purified by passage through a Sephadex G-15 column (Pharmacia). Addition of equimolar cupric acetate, followed by lyophilization, produces the active molecule.

EXAMPLE 5

Stomach ulcers were induced in rats by the Shay procedure. Briefly stated, the passage between the stomach and the intestine in the rat is tied off, thereby causing a buildup of stomach acid, resulting in ulceration. For treatment, the rats received 10 mg of GHL or GHL-Cu or a derivative thereof in 0.25 ml saline intubated into the stomach. Control rats received saline only. After 24 hours, the stomachs were photographed and the stomach acidity determined.

The results of the experiments are shown in the following table, which depicts the inhibition of stomach acid accumulation and stimulation of cytoprotective mucous secretion in the rats. The mucous production was visually rated from 0 to ++++, where 0 represented substantially no mucous observed and ++++ represented a very heavy mucous secretion.

TABLE

| | Stomach Acidity pH ± standard deviation | Mucous Production |
|---|---|---|
| Control | 2.01 ± 0.27 | Unobservable |
| GHL | 3.26 ± 0.47 | ++ |
| GHL + GHL-Cu | 6.52 ± 0.70 | ++++ |
| GHL-Cu | 6.94 ± 0.25 | ++++ |

Further, as shown in the FIGURE, the treatment of rats with GHL-Cu markedly reduced the formation of stomach ulcers.

From the foregoing it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for reducing the secretion of stomach acid in warm-blooded animals, comprising:
   administering to the animal a therapeutically effective amount of a composition comprising glycyl-L-histidyl-L-lysine.

2. A method for reducing the secretion of stomach acid in warm-blooded animals, comprising:
   administering to the animal a therapeutically effective amount of a composition comprising glycyl-L-histidyl-L-lysine: copper(II).

3. A method for reducing the secretion of stomach acid in warm-blooded animals, comprising:
   administering to the animal a therapeutically effective amount of a derivative of GHL-Cu having the general formula:

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

4. A method for reducing the secretion of stomach acid in warm-blooded animals, comprising:
   administering to the animal a therapeutically effective amount of a derivative of GHL-Cu having the general formula:

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

5. A method for increasing the secretion of cytoprotective mucous in the stomach of warm-blooded animals, comprising:
   administering to the animal a therapeutically effective amount of a composition comprising glycyl-L-histidyl-L-lysine.

6. A method for increasing the secretion of cytoprotective mucous in the stomach of warm-blooded animals, comprising:
   administering to the animal a therapeutically effective amount of a composition comprising glycyl-L-histidyl-L-lysine: copper(II).

7. A method for increasing the secretion of cytoprotective mucous in the stomach of warm-blooded animals, comprising:
   administering to the animal a therapeutically effective amount of a derivative of GHL-Cu having the general formula:

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

8. A method for increasing the secretion of cytoprotective mucous in the stomach of warm-blooded animals, comprising:
   administering to the animal a therapeutically effective amount of a derivative of GHL-Cu having the general formula:

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

9. A method for reducing the formation of stomach ulcers in warm-blooded animals, comprising:
administering to the animal a therapeutically effective amount of a composition comprising glycyl-L-histidyl-L-lysine.

10. A method for reducing the formation of stomach ulcers in warm-blooded animals, comprising:
administering to the animal a therapeutically effective amount of a composition comprising glycyl-L-histidyl-L-lysine: copper(II).

11. A method for reducing the formation of stomach ulcers in warm-blooded animals, comprising:
administering to the animal a therapeutically effective amount of a derivative of GHL-Cu having the general formula:

wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

12. A method for reducing the formation of stomach ulcers in warm-blooded animals, comprising:
administering to the animal a therapeutically effective amount of a derivative of GHL-Cu having the general formula:

wherein X is glycyl-L-alanyl, glycyl-L-seryl, or glycyl-L-valyl, and wherein R is selected from the group consisting of alkyl moieties containing from 1 to 18 carbon atoms, aryl moieties containing from 6 to 12 carbon atoms, alkoxy moieties containing from 1 to 12 carbon atoms, and aryloxy moieties containing from 6 to 12 carbon atoms, or where R is L-prolyl-L-valyl-L-phenylalanyl-L-valine or L-valyl-L-phenylalanyl-L-valine.

* * * * *